(12) United States Patent
Caspers (10) Patent No.: US 8,114,167 B2
(45) Date of Patent: Feb. 14, 2012

(54) DYNAMICALLY ACTIVATED VARIABLE RESPONSE SOCKET TECHNOLOGY

(75) Inventor: Carl A. Caspers, Waite Park, MN (US)

(73) Assignee: Carl Caspers Consulting LLC, Sartell, MN (US)

( * ) Notice: Subject to any disclaimer, the term of this patent is extended or adjusted under 35 U.S.C. 154(b) by 188 days.

(21) Appl. No.: 12/477,572

(22) Filed: Jun. 3, 2009

(65) Prior Publication Data

US 2010/0312359 A1 Dec. 9, 2010

(51) Int. Cl.
*A61F 2/80* (2006.01)
(52) U.S. Cl. .......................................... 623/34
(58) Field of Classification Search ............... 623/32–38
See application file for complete search history.

(56) References Cited

U.S. PATENT DOCUMENTS

| | | | |
|---|---|---|---|
| 5,258,037 A | 11/1993 | Caspers | |
| 5,376,132 A | 12/1994 | Caspers | |
| 5,534,034 A | 7/1996 | Caspers | |
| 5,549,709 A | 8/1996 | Caspers | |
| 5,571,208 A | 11/1996 | Caspers | |
| 5,735,906 A | 4/1998 | Caspers | |
| 5,904,722 A | 5/1999 | Caspers | |
| 5,931,872 A | 8/1999 | Lohmann | |
| D429,335 S | 8/2000 | Caspers et al. | |
| 6,508,842 B1 | 1/2003 | Caspers | |
| 6,554,868 B1 | 4/2003 | Caspers | |
| 6,645,253 B2 | 11/2003 | Caspers | |
| 6,726,726 B2 | 4/2004 | Caspers | |
| 6,761,742 B2 | 7/2004 | Caspers | |
| 6,926,742 B2 | 8/2005 | Caspers et al. | |
| 6,974,484 B2 | 12/2005 | Caspers | |
| 7,150,762 B2 | 12/2006 | Caspers | |
| 2002/0099450 A1 | 7/2002 | Dean et al. | |
| 2005/0149202 A1 | 7/2005 | Schaffer et al. | |
| 2007/0055383 A1 | 3/2007 | King | |
| 2007/0196222 A1 | 8/2007 | Mosler et al. | |
| 2008/0221706 A1 | 9/2008 | Scussel et al. | |

FOREIGN PATENT DOCUMENTS

| | | |
|---|---|---|
| WO | WO 00/23016 A1 | 4/2000 |
| WO | WO 02/067825 A2 | 9/2002 |
| WO | WO 2004/071337 A2 | 8/2004 |
| WO | WO 2008/033337 A2 | 3/2008 |

*Primary Examiner* — Bruce E Snow
(74) *Attorney, Agent, or Firm* — Gerald E. Helget; Nelson R. Capes; Briggs and Morgan, P.A.

(57) ABSTRACT

A socket system in an artificial limb for amputees, the socket system being dynamically activated by weight-bearing loads and variable in response to shear forces imposed by weight-bearing loads. The socket system includes: a liner adapted to engage the residual limb; a semi-flexible inner socket having a textured surface; an inner socket air wick between the liner and the textured surface of the inner socket; a semi-rigid outer socket having a textured surface; an outer socket air wick between the inner socket and the textured surface of the outer socket; a sealing sleeve engaging the outer socket and the residual limb, the sealing sleeve, the outer socket, and the residual limb creating a sealed chamber; and a vacuum source connected to the sealed chamber and creating a vacuum within the sealed chamber. The vacuum source is dynamically activated in response to weight-bearing loads and varies the response of the socket system to shear forces imposed by weight-bearing loads. The socket system may alternatively be a single rigid socket with a flexible brim.

14 Claims, 5 Drawing Sheets

Fig.6 Valgus Torque (PRIOR ART)

Fig.10 Valgus Torque

DYNAMICALLY ACTIVATED VARIABLE RESPONSE SOCKET TECHNOLOGY

BACKGROUND OF THE INVENTION

The present invention relates to prosthetic and orthotic devices and more particularly to a dynamically activated, variable-response prosthetic or orthotic socket system.

An amputee is a person who has lost part of an extremity or limb such as a leg or arm which commonly may be termed as a residual limb. Residual limbs come in various sizes and shapes with respect to the stump. That is, most new amputations are either slightly bulbous or cylindrical in shape while older amputations that may have had a lot of atrophy are generally more conical in shape. Residual limbs may further be characterized by their various individual problems or configurations including the volume and shape of a stump and possible scar, skin graft, bony prominence, uneven limb volume, neuroma, pain, edema or soft tissue configurations.

Figures 1, 2:
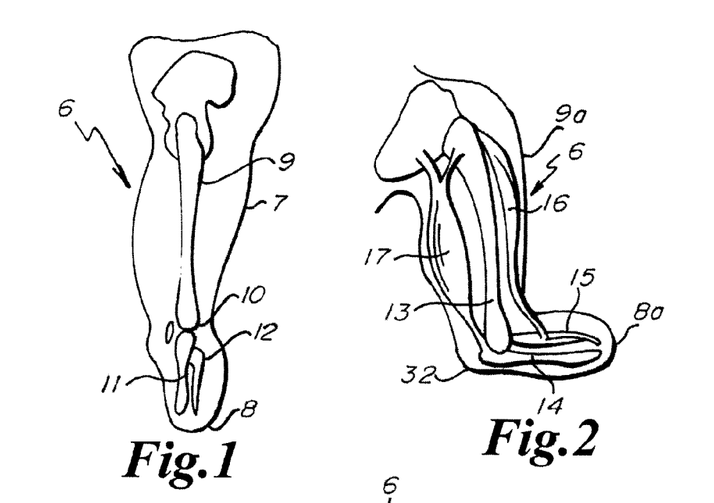
FIG. 1 is a side elevational view of the tissue and skeletal structure of an amputee's residual limb.
FIG. 2 is a side elevational view of a residual limb in the form of an amputated arm showing the skeletal and muscular structure of the residual limb.

Referring to FIGS. 1 and 2, a below the knee residual limb 6 is shown and described as a leg 7 having been severed below the knee terminating in a stump 8. In this case, the residual limb 6 includes soft tissue as well as the femur 9, knee joint 10, and severed tibia 11 and fibula 12. Along these bone structures surrounded by soft tissue are nerve bundles and vascular routes which must be protected against external pressure to avoid neuromas, numbness and discomfort as well as other kinds of problems. A below the knee residual limb 6 has its stump 8 generally characterized as being a more bony structure while an above the knee residual limb may be characterized as including more soft tissue as well as the vascular routes and nerve bundles.

Referring to FIG. 2, amputees who have lost a part of their arm 9a, which terminates in a stump 8a also may be characterized as having vascular routes, nerve bundles as well as soft and bony tissues. The residual limb 6 includes the humerus bone 13 which extends from below the shoulder to the elbow from which the radius 14 and ulna 15 bones may pivotally extend to the point of severance. Along the humerus bone 13 are the biceps muscle 16 and the triceps muscle 17 which still yet may be connected to the radius 14 and the ulna, 15, respectively.

In some respects, the residual limb amputee that has a severed arm 9a does not have the pressure bearing considerations for an artificial limb but rather is concerned with having an artificial limb that is articulable to offer functions typical of a full arm, such as bending at the elbow and grasping capabilities. An individual who has a paralyzed limb would also have similar considerations wherein he or she would desire the paralyzed limb to having some degree of mobility and thus functionality.

Historically, artificial limbs typically used by a leg amputee were for the most part all made out of wood such as an Upland Willow. The limbs were hand carved with sockets for receiving the stump of the residual limb. Below the socket would be the shin portion with the foot below the shin. These wooden artificial limbs were covered with rawhide which often were painted. The sockets of most wood limbs were hollow as the limbs were typically supported in the artificial limb by the circumferential tissue adjacent the stump rather than at the distal end of the stump.

Some artificial limbs in Europe were also made from forged pieces of metal that were hollow. Fiber artificial limbs were also used which were stretched around a mold after which they were permitted to dry and cure. Again, these artificial limbs were hollow and pretty much supported the residual limb about the circumferential tissue adjacent the stump.

All of these various artificial limbs have sockets to put the amputee's stump thereinto. There are generally two categories of sockets. There are hard sockets wherein the stump goes right into the socket actually touching the socket wall without any type of liner or stump sock. Another category of sockets is a socket that utilizes a liner or insert. Both categories of sockets typically were opened ended sockets where they had a hollow chamber in the bottom and no portion of the socket touched the distal end of the stump. So, the stump was supported about its circumferential sides as it fits against the inside wall of the sockets.

These types of sockets caused a lot of shear force on the stump as well as had pressure or restriction problems on the nerve bundles and vascular flow of fluid by way of the circumferential pressure effect of the socket on the limb. This lack of contact pressure effect could cause a swelling into the ends of the socket where an amputee may develop severe edema and draining nodules at the end of their stump.

With time, prosthetists learned that by filling in the socket's hollow chamber and encouraging a more total contact with the stump and the socket, the swelling and edema problems could be eliminated. However, the problematic tissue configurations, and bony prominences, required special consideration such as the addition of soft or pliable materials to be put into the socket.

Today, most artificial limbs are constructed from thermoset plastics such as polyester resins, acrylic resins, polypropylenes and polyethylenes, which are perhaps laminated over a variety of textiles which are impregnated by the various resins.

In the past, most artificial limbs were suspended from the amputee's body by some form of pulley, belt or strap suspension often used with various harnesses and perhaps leather lacers. Another method of suspending artificial limbs is known as the wedge suspension wherein an actual wedge is built into the socket which is more closed at its top opening. The wedge in the socket cups the medial femoral condyle or knuckle at the abductor tubical. Yet another form of suspension is referred to as the shuttle system or a mechanical hookup or linkup wherein a thin suction liner is donned over the stump that has a docking device on the distal end which mechanically links up with its cooperative part in the bottom of the socket chamber. Sleeve suspensions were also used wherein the amputee would roll on over both the top of the artificial limb and onto the amputee's thigh. The sleeve suspensions have been used in combination with other forms of suspensions techniques.

Both the use of a positive pressure system and the use of a negative pressure system (or hypobaric closed chamber) have been utilized in the field of prosthetics. At one time, for pressure systems "inflatable inner tubes" were used to fit into sockets. Presently, there are pneumatic "bags" which are strategically placed over what people consider to be good weight-bearing areas to increase pressure to help accommodate for volume changes within the socket.

The problem with this is that higher pressure areas cause more volume losses and this very specific pressure creates atrophy and loss of tissue dramatically over these high pressure areas. None of these systems employs positive pressure distributed over the entire total contact area between the residual limb and the artificial limb socket to accommodate volume changes within the socket.

The negative pressure aspects have been utilized for a closed chamber in that a socket is donned by pulling in with a sock, pulling the sock out of the socket and then closing the opening with a valve. This creates a seal at the bottom and the stump is held into the socket by the hypobaric seal.

The older systems were initially started in Germany. They were an open-ended socket, meaning there was an air chamber in the bottom of the socket. This did not work particularly well because it would cause swelling of the residual limb into the chamber created by the negative draw of suspending the weight of the leg and being under a confined area. This would lead to significant edema which would be severe enough to cause stump breakdown and drainage.

It was later discovered in America that total contact was essential between the residual limb and the socket and once you had total contact the weight was distributed evenly or the suspension was distributed over the whole surface of the limb rather than just over the open chamber portion of the socket.

The use of vacuum to suspend the artificial limb from the residual limb is known and is illustrated in U.S. Pat. No. 6,726,726, herein incorporated by reference.

The human body as a whole is under approximately one atmosphere of pressure at sea level. It keeps and maintains a normal fluid system throughout the body. When an amputee dons a prosthesis and begins taking the pressures of transmitting the weight of the body through the surface area of the residual limb to the bone, there is increased pressure on the residual limb equal to one atmosphere plus whatever additional pressures are created by weight bearing. This increased pressure causes the eventual loss of fluids within the residual limb to the larger portion of the body which is under less pressure. This loss of fluids causes the volume of the residual limb to decrease during the day. It varies from amputee to amputee, but it is a constant among all amputees and the more "fleshy" and the softer the residual limb, the more volume fluctuation there will be. The greater the weight and the smaller the surface area, the greater the pressures will be and the more "swings" there will be in fluids. In the past, the amputee had to compensate for this volume decrease by removing the artificial limb and donning additional stump socks to make up for the decreased residual limb volume.

The human body utilizes a skeletal system to support its mass and weight. None of its remaining systems were designed to support its mass or weight other than the fat pads on the plantar surface of the feet. These fat pads were especially designed to support the weight and mass of the body without losing their fluid content or volume. All remaining tissue is susceptible to loads greater than atmospheric pressure, less than atmospheric pressure, high mechanical pressure, hydration levels, and general vascular and neurological health.

Previous and current socket technologies have always been a rigid support structure that is static in nature and has no way to compensate for limb volume change, changes in tissue load requirements, or concentric or eccentric joint motion which alters the physiological shape of the joint and surrounding soft tissue They have never utilized dynamic response socket technology to compensate for volume and eccentric and concentric joint changes through range of motion of the joint. The utilization of vacuum to date, for example, in U.S. Pat. No. 6,726,726, has only been in the suspension of the artificial limb and has not been utilized in the stabilization and support of vertical tangent and rotational weight bearing loads which are more significant than suspension. For example, the '726 patent discloses vacuum being applied to a cavity between an inner socket and a polyurethane liner to draw the residual limb, encased in the polyurethane liner, against the inner socket to suspend the prosthetic limb from the residual limb. The '726 patent does not, however, disclose the use of a semi-flexible inner socket or a semi-rigid outer socket with a textured surface area available for countering vertical tangent and rotational forces, and accommodating both positive and negative pressures.

Static sockets are unable to compensate for limb volume changes created by loads greater than atmospheric pressure, less than atmospheric pressure, or high mechanical pressure. At present, there is only one item within the confines of the prosthetic socket that has any dynamic response capabilities: a specially formulated urethane interface or liner, also disclosed in U.S. Pat. No. 6,726,726 and incorporated by reference. All other interface media such as TPE or silicone or expanded foam materials do not possess this dynamic characteristic. However, even with this dynamic characteristic, urethane is unable to compensate for many of the socket-created issues.

For example, vacuum's strongest holding force is perpendicular to the surface that it is applied to. About ninety percent of the vertical load forces in a socket are tangent and not perpendicular and therefore vacuum is significantly reduced in its ability to control vertical tangent and rotational loads and distal migration of the limb in the socket. Furthermore, a urethane socket liner has a tendency to flow out of the brim of the socket, and thus become thinner, when subjected to weight-bearing pressures.

An additional problem with laminated sockets is that vacuum leaks out of them, and it therefore necessary for the vacuum to be continually renewed. While sockets of molded thermoplastics do not leak like laminated sockets, and do not absorb moisture, it is difficult to mold the thermoplastic socket with uniform wall thickness.

Skin Physiological Principles

Atmospheric pressure (1 atm=~14.7 psi) is constantly compressing us from all directions. This may not sound like much, but consider that this compressive pressure over the surface of the average body (~3,000 in$^2$) totals ~44,000 lbs of force! The blood and lymphatic vascular systems are well adapted to this large compressive pressure. The tissue pressure throughout our body is only slightly (<0.2%) less than the external atmospheric pressure (Guyton and Hall, Textbook of Medical Physiology). In this pressurized environment the blood capillaries are constantly delivering water and nutrients to all tissues and the blood and lymphatic capillaries remove excess water and wastes from the tissues to sustain a healthy fluid environment in which the cells are bathed.

This homeostatic condition is disturbed when external pressure deviates from 1 atm. The body easily adapts to the daily fluctuations in atmospheric pressure. It can also withstand greater increases or decreases in external pressure for limited amounts of time. However, as seen with amputees, skin health suffers if these deviations from 1 atm are large enough, transition sharply enough or are applied long enough. This is true for pressures above 1 atm and below 1 atm.

For example, high pressures over a bony prominence can cause skin to break down. Sub atmospheric pressure can also lead to skin damage. For example, the distal end of the limb will swell and some of its capillaries rupture if it is leveraged off the bottom of a sealed socket sufficiently hard or for an extended period of time.

Problem Area

With the traditional rigid socket and vacuum suspension, conditions often exist at the brim where the pressures exceed 1 atm and fall below 1 atm.

High Pressure at Brim

The limb experiences high pressure when it is pressed against a rigid brim. This usually occurs under two conditions: 1) the leg leverages in the socket, driving the proximal end of the limb against the edge of the socket brims or 2) the limb slides toward the brim (e.g. wide posterior aspect of the femoral condyles slides forward during knee flexion, wedging it between the narrowing anterior brims). This elevated pressure can lead to ischemia, discomfort, pain, skin breakdown and/or chronic soft tissue atrophy.

Low Pressure

Low pressures at the brim are always due to a slight separation between the liner and skin. This expansion of the trace air space between the skin and the liner decreases pressure between the skin and liner. The skin moves towards the low pressure to fill this space, causing edema and/or dermal capillary bleeding if the pressure drop in the uncontained space is large enough or is applied for an extended period of time.

This space is created by the following sequence of events:

1) The limb and rigid socket are pulled apart (e.g. knee extension leverages the knee away from the rigid brim).

2) This expands the air space between the liner and socket causing a void of low pressure. This is the vacuum space, so it is already under low pressure and the gapping further lowers the pressure.

3) The liner moves towards this low pressure void (towards the socket).

4) As the liner moves towards the socket, it increases the trace space between the liner and skin. This creates a second low pressure space, this one being between the skin and liner.

5) The skin likewise attempts to fill this low pressure void by moving towards the displaced liner.

6) The pressure in the interstitial space (within the soft tissues of the limb), in turn, drops causing greater blood capillary filtration and potential blood capillary rupture. Filtration is leaking of blood plasma (92% water) out of the capillaries and into the interstitial space.

It should be noted in step 3 that the extent to which the liner moves towards the socket will be determined by equilibration of the low pressures in the two voids. When the low pressures in the voids on either side of the liner equilibrate, liner movement will cease.

Figure 3:
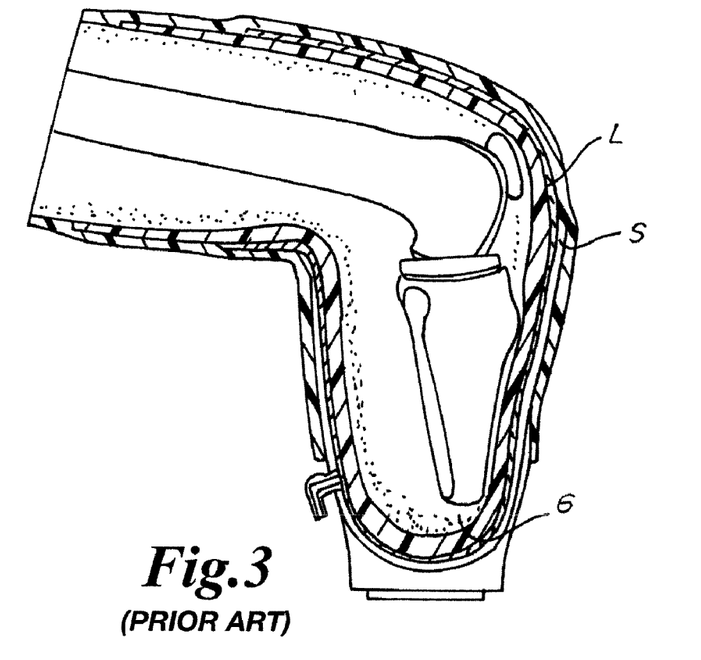
FIGS. 3-6 are schematic cross-sectional views of prior art socket structures.
Figure 4:
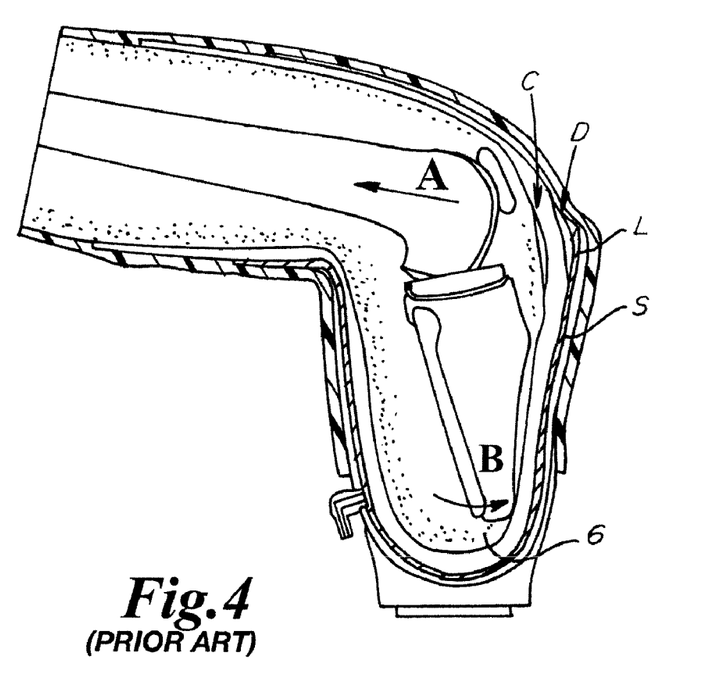

An example of these steps is illustrated in FIGS. 3 and 4. In FIG. 3, the liner L is in its normal position, "sandwiched" between the limb 6 and rigid socket S. The change in FIG. 4 is that the knee has moved back (A) as the tibia was pressed against the bottom of the socket (B). In this example this occurred because the amputee tried to extend the knee. This leveraging led to the sequence of events listed above, causing low pressure voids at C and D.

Figures 5, 6:
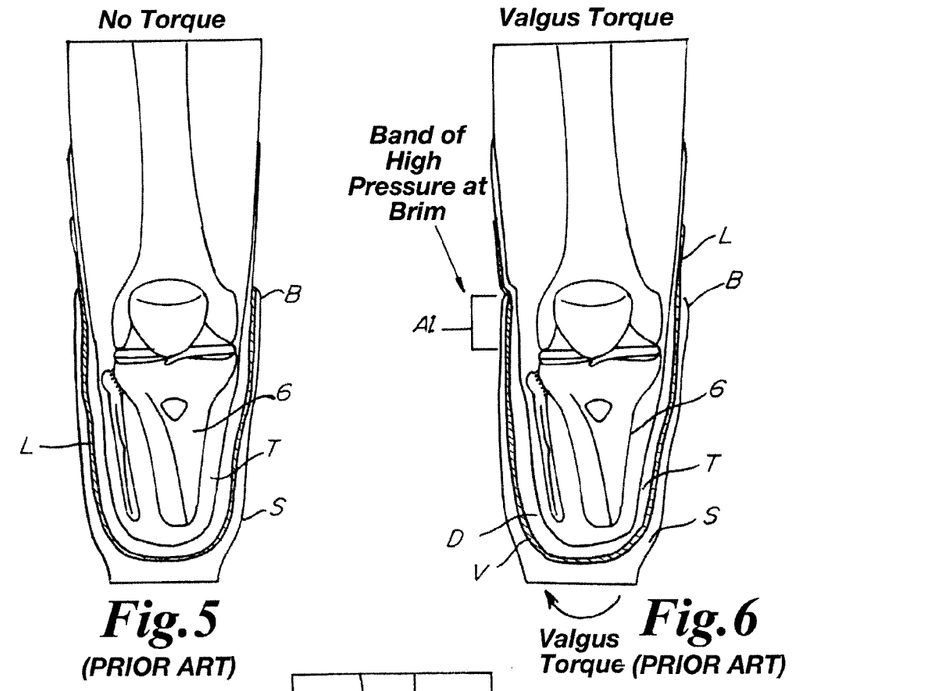

When a torque is applied to a traditional rigid socket (S), the socket rotates as it compresses the liner (L) and soft tissues (T) of the leg. On one side of the leg the brim (B) is driven against the limb proximally. This creates a fairly narrow bank of high pressure at the brim. As shown in FIG. 6, when a valgus torque (clockwise in this view) is applied to the socket, the top of the lateral aspect of the socket is driven into the liner and limb, creating a band of high pressure. The pressure is relatively high because of the small surface area (A1) between the top of the socket and liner. Notice that the distal, lateral (D) end of the limb (6) tends to pry away from the socket creating a void V.

Figure 10:
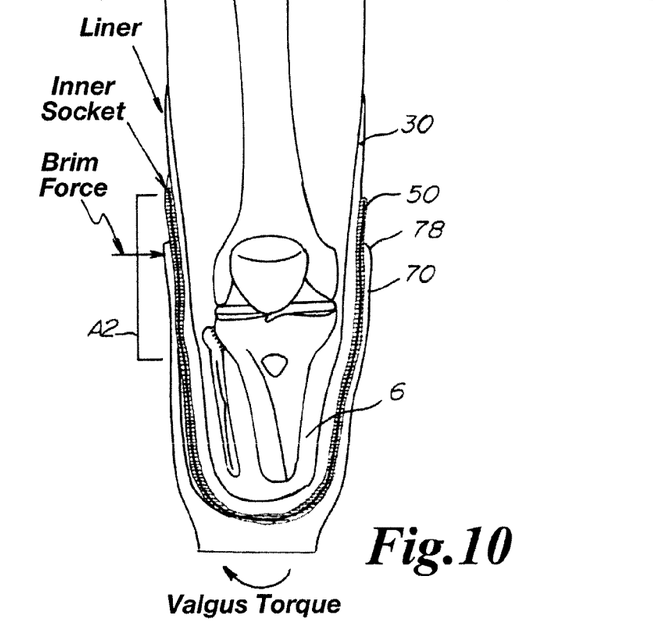
FIG. 10 is a schematic cross-sectional view of an embodiment of the present invention.

The "flexible" inner socket (50) decreases the previously described peak pressures by distributing the brim force over a larger surface area. As shown in FIG. 10, as the brim (78) of the outer socket (70) is driven against the inner socket (50), the inner socket (50) distributes the brim force over a large surface area (A2) of the liner (30). This is much the same principle as a soccer shin guard that has a pliable yet stiff outer shell (equivalent to the inner socket) that when kicked (equivalent to the brim force) distributes the kicking force across the underlying padding (equivalent to the liner) more uniformly to the shin (equivalent to the stump).

SUMMARY OF THE INVENTION

The subject invention includes a vacuum-managed, dynamically activated, variable-response prosthetic and orthotic sockets. The following provides a discussion of the objects and advantages of the subject invention.

1. Double Socket Structure with Textured Surfaces.

To improve the capability of vacuum to counter vertical weight-bearing loads which shear against the socket wall, in one embodiment the subject invention has two sockets: an inner, semi-flexible socket and an outer, semi-rigid socket. The interior surface and exterior surface of the inner socket are preferably textured to increase surface area and friction holding capability. Either the inner surface of the inner socket or the outer surface of the inner socket or both may be textured. The interior surface of the outer socket may also be textured to increase the surface area and friction holding capability. The exterior surface of the liner and fabric overcovering may also optimized to improve shear linkage capability. For example, an external matrix over-liner may be provided to facilitate and enhance linkage between the liner and internal socket members. Enhancing the linkage between the liner and the inner socket reduces the distal vertical migration of the residual limb during weight bearing by controlling characteristics of the urethane liner. Because of the enhanced shear linkage capability, the urethane liner remains in the inner socket and does not flow out of the socket under weight-bearing pressures. The enhanced shear-linkage also gives maximum suspension and load bearing characteristics to the socket environment. As many amputees' residual limbs do not have adequate surface area for weight bearing, it becomes paramount to utilize all available surface to reduce as much as possible the load forces being applied to the residual limb. The available surface area is increased by the texturing of the socket surfaces.

An air wick is present between the urethane liner and the inner socket, and a second air wick is present between the inner socket and the outer socket. An external suspension sleeve seals both the inner and the outer sockets to the residual limb and creates a sealed chamber containing the outer and inner sockets and air wicks, to which vacuum is applied. The vacuum causes the air wicks to be tightly drawn into the textured surfaces of the sockets, thus dramatically increasing the shear linkage between these components. Furthermore, the vacuum creates an "I-beam"-like structure from the outer socket, the inner socket, and the air wick to increase the ability of these components to be made thinner and more flexible with increased dynamic response capability and yet sufficiently strong for weight bearing loads.

The inner, semi-flexible socket also changes shape under weight-bearing loads to accommodate changes in the residual limb by degrees of dynamic response. For example, the inner, semi-flexible socket may respond dynamically to change its rotary shape and to change its vertical load shape.

2. Single Socket with Flexible Brim.

Figure 9:
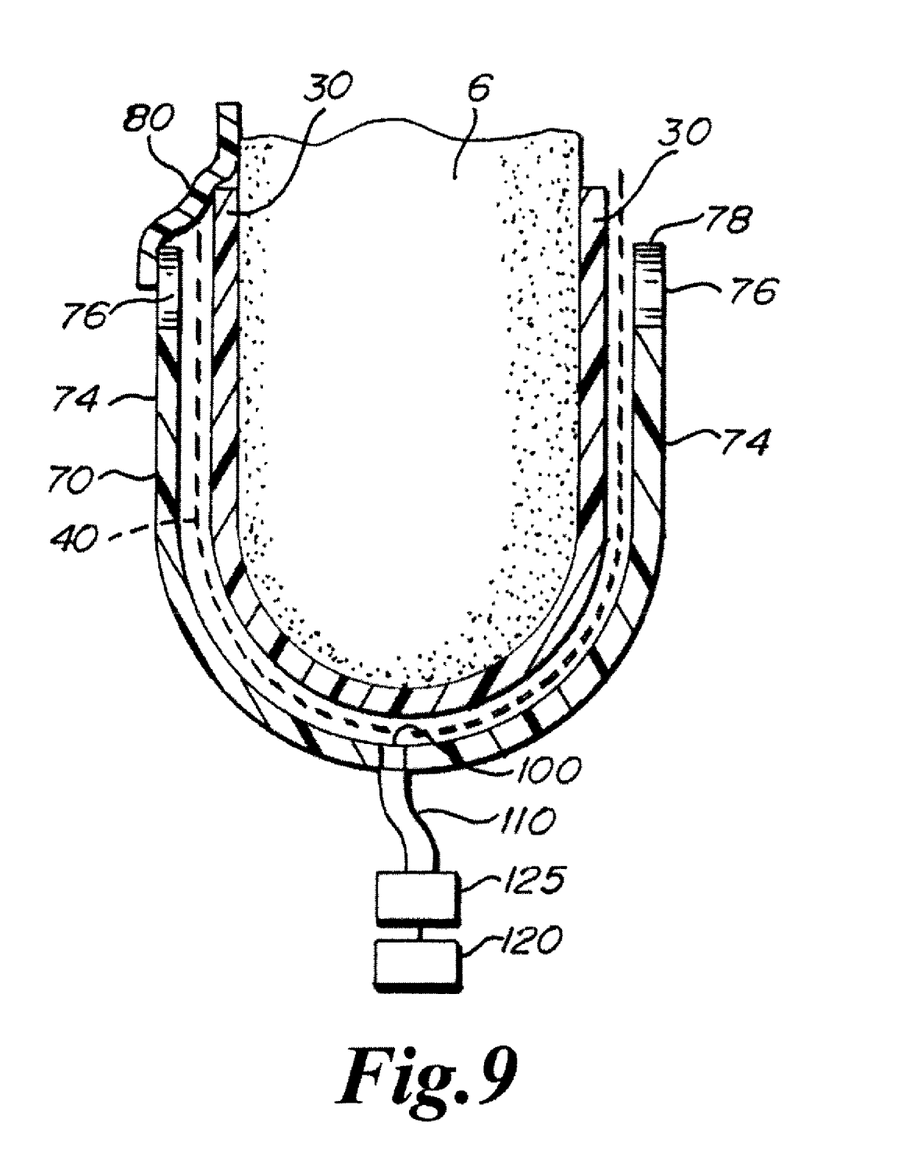
FIG. 9 is a schematic cross-sectional view of a second embodiment of the subject invention.

In a second embodiment, the subject invention has a single, rigid socket that further comprises a stiff portion and a less stiff or flexible portion proximate the brim f the socket. The stiffness of the flexible brim portion of the socket is sufficient to: 1) reduce the sharp high pressure line A1 previously discussed in FIG. 9 when the limb is driven against the rigid brim of previous designs, and 2) follow the limb when it is pulled away from the socket, avoiding low pressure voids previously illustrated in FIG. 7.

Objects and Advantages of the Present Invention.

A principle object and advantage of the present invention is to improve the capability of vacuum to counter vertical weight bearing loads which shear against the socket wall.

Another principle object and advantage of the present invention is to enhance the linkage between the liner and the inner socket to reduce the distal vertical migration of the residual limb during weight bearing.

A feature of the present invention is an inner socket air wick between the urethane liner and the inner socket, the inner socket having a textured surface to increase the coefficient of friction between it and the air wick.

Another feature of the present invention is an outer socket air wick between the inner socket and the outer socket, the outer socket having a textured surface to increase the coefficient of friction between it and the air wick.

Another principle object and advantage of the present invention is that the semi-flexible inner socket may change shape under weight bearing loads to accommodate changes in the residual limb.

Another principle object and advantage of the present invention is a single socket with a flexible brim portion that reduces the sharp high pressure caused by the limb being driven against the brim.

Another principle object and advantage of the present invention is that the flexible brim portion permits the flexible brim to follow the limb when the limb is pulled away from the socket, thus avoiding low pressure voids.

DETAILED DESCRIPTION OF PREFERRED EMBODIMENT

1. Double Socket Structure with Textured Surfaces.

Figure 7:
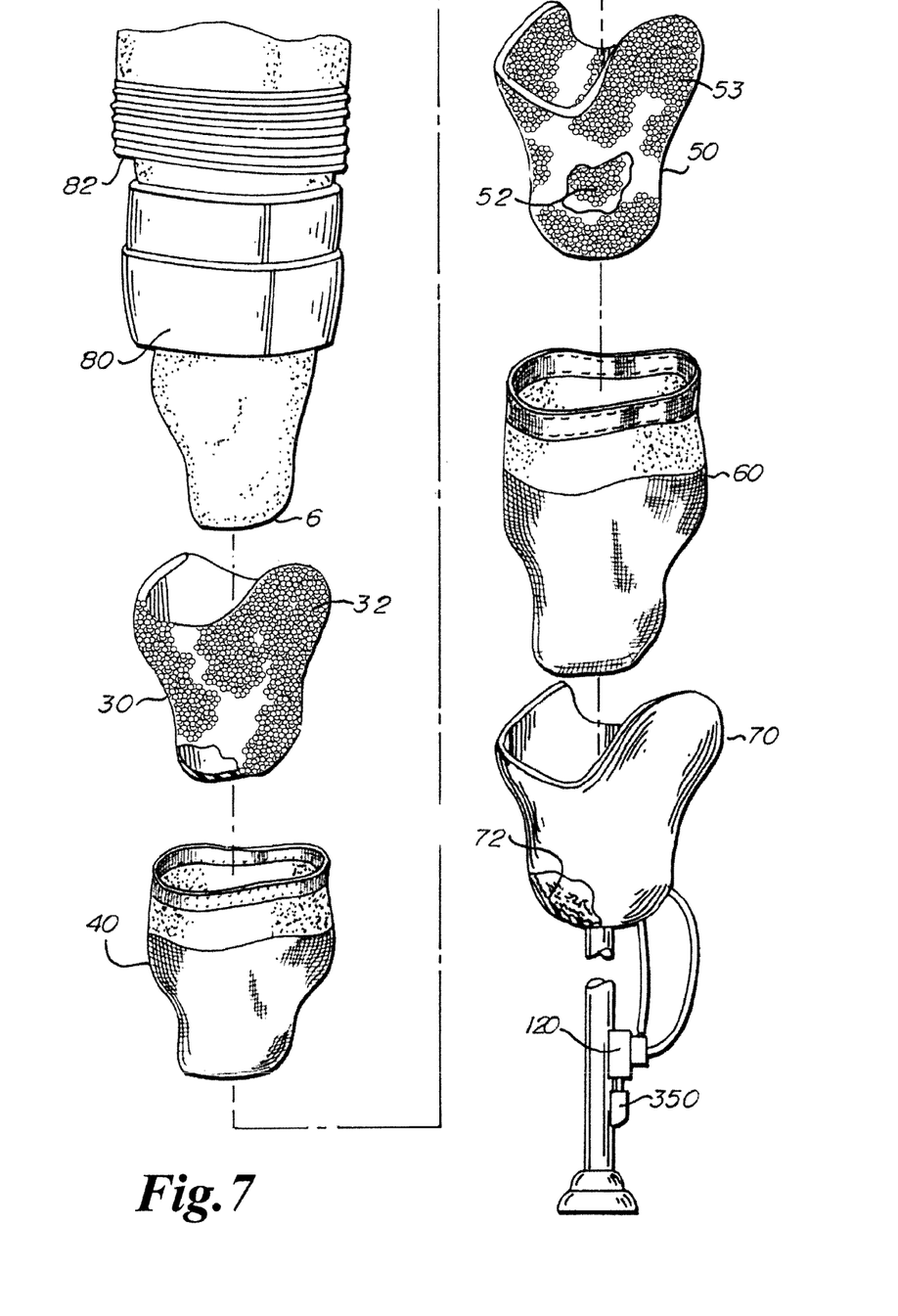
FIG. 7 is an exploded elevational view of the residual limb donning the components of the subject invention.
Figure 8:
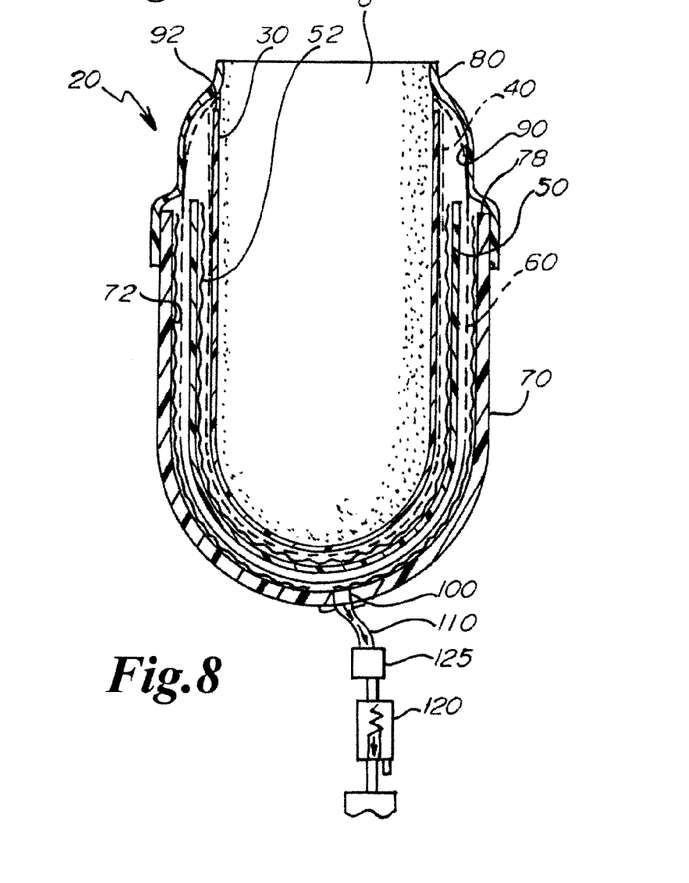
FIG. 8 is a schematic cross-sectional view of a first embodiment of the subject invention.

Referring to FIGS. 7 and 8, a first embodiment of the subject invention having a double socket structure with textured surfaces is described.

In the first embodiment illustrated, the subject invention is a dynamically-activated, variable-response artificial limb socket system 20 comprising (working outwards from the residual limb 6): a liner 30, an inner socket air wick 40, an inner socket 50, an outer socket air wick 60, an outer socket 70, and a sealing sleeve 80. The inner socket 50 preferably has a textured inner surface 52 opposing the inner socket air wick 40. The outer socket 70 preferably has a textured inner surface 72 opposing the outer socket air wick 60.

Optionally, the inner socket 50 may have a textured outer surface 53 opposing the outer socket air wick 60, as shown in FIG. 7.

FIG. 7 also illustrates that the liner 30 may have a textured surface 32 facing the inner socket air wick 40.

The sealing sleeve 80 seals against the outer socket 70 and the residual limb 20, forming a space 90 containing the outer socket 70, the outer socket air wick 60, the inner socket 50, and the inner socket air wick 40.

A vacuum port 100 communicates with the space 90. A vacuum line 110 communicates with the vacuum port 100 and with a vacuum source 120 through a check valve 125.

The textured surfaces 52, 53 of the inner socket 50 may be formed by any process which increases the coefficient of sliding friction between the (typically smooth) inner socket 50 and the inner socket air wick 40. An example, without limitation, would be to embed a thin mesh in the inner socket 52 during the manufacturing process, so that the mesh forms the textured surfaces 52, 53. A similar process would be used to create the textured inner surface 72 of the outer socket 70. Applicant has found that this texturing increases the surface area of the inner socket 50 engaging the inner socket air wick 40 and the surface area of the outer socket 70 engaging the outer socket air wick 60, as well as the coefficient of sliding friction of the inner and outer sockets. A relationship between these surface areas and the holding force Fs that will be developed when a difference in pressure is applied to the space 90 can be described by the formulas:

$$Fs = Fp + Ff$$

Where:
Fs = the suspension force.
Fp = the force due to the pressure difference between the inside and the outside of the space 90.
Ff = the friction force between the side walls of the socket and the textured surface.

$$Fp = Ps \cdot Acs.$$

Where:
Fp = the force due to the pressure difference between the inside and outside of the space 90.
Ps = the measure of the sub-atmospheric pressure (vacuum) in the space 90. In terms of absolute pressure, Ps is the difference in pressures outside the space (atmospheric pressure) and inside the space.
Acs = the cross sectional area of the limb/liner at the height of the seal.

$$Ff = N \cdot us.$$

Where:
Ff = the maximal frictional force between the side walls of the socket and the textured surface.
N = the normal (perpendicular) force between the socket side walls and the textured surface.
us — the coefficient of maximal static friction.

This normal force in a vacuum system with the artificial limb "hanging" on the residual limb is:

$$N = Ps \cdot Asw.$$

Ps = the vacuum level as previously defined.
Asw = the surface area of the side walls of the socket.
Substitution of equations as above yields:

$$Fs = Ps \cdot Acs + Ps \cdot Asw \cdot us.$$

A sample calculation is as follows, assuming Ps=11.25 psi (or 23 inches Hg); Acs=13.5 square inches; Asw=17.1 square inches:

$$Fs = 11.25 \text{ psi} \cdot 13.5 \text{ in}^2 + 11.25 \text{ psi} \cdot 17.1^2 \cdot 0.5.$$

$$Fs = 152 \text{ lbs} + 96 \text{ lbs}.$$

$$Fs = 248 \text{ lbs}.$$

It should be noted also that the pressure differential component (152 lb.) of the suspension force exists regardless of the size of the extraction force acting on the socket. In contrast, friction will tend to remain at zero until the socket extraction force exceeds 152 lb., at which time friction will increase up to 96 lb to counter the increasing extraction force. Note that these calculations and discussion only apply to the axial suspension force (Fs).

If all forces remain perpendicular, the coefficient of static friction does not come into play. If vertical, tangent and rotational moments are part of the load forces then the coefficient of static friction becomes a major controlling factor.

For example, if one had a suction cup like the one used to carry sheets of glass, the larger the square surface area of the seal on the glass the greater the perpendicular holding capability would be. If there were (0) zero coefficient of static friction between the glass and the suction cup and one applied a vertical loading force, the glass would slide right on the suction cup.

The reader will understand that if the normal weight bearing force is known, the socket may be designed to have adequate surface area to support those load forces under a given vacuum level and coefficient of static friction. Alternatively, if the surface area of the residual limb 20 is not sufficient, the vacuum supplied to the chamber 90 may be increased or the coefficient of static friction could be increased, for example, by increasing the texture of the textured surfaces 52 and 72.

The outer socket air wick 60 extends proximally to join with the inner socket air wick 40. Both air wicks reside on the outside of the liner 30 terminating, without limitation, approximately 1½" from the proximal edge 92 of the liner. The sealing sleeve 80 resides on the exterior of the outer socket 70, continues proximally over both inner and outer air wicks and the inner socket 50 and onto approximately the last 1½" of the liner 30, coming to rest on the patient's skin, sealing the whole socket system. Vacuum from the vacuum source 120 is then applied to both inner and outer air wicks to combine all socket components into one dynamic variable response socket system. Both inner and outer socket surfaces may be textured to optimize linkage between the inner and outer sockets and other components. The utilization of vacuum not only provides greatly improved suspension of the prosthesis but also dramatically improves vertical load bearing and rotational stability within the socket environment as well as managing the liner flow characteristics.

When vacuum is applied as described above, the inner socket 50, the outer socket air wick 60, and the outer socket 70 form structurally an I-beam-like structure that has improved strength but less weight and bulk. This allows the inner and outer sockets to be more dynamic in nature and to be very strong.

The inner socket 50 and outer socket 70 may be designed to change shape under weight bearing loads to accommodate changes in the residual limb shape and load requirements.

For example, the inner socket 50 may be described as "semi-flexible," meaning that is more flexible than rigid. The outer socket 70 may be described as "semi-rigid," meaning that it is more rigid than flexible.

Materials that may be used for the inner and outer sockets may include, without limit: Material No. 616T52 (ThermoLyn rigid polystyrene); Material No. 616T39 (ThermoLyn Flexible ionomer); Material No. 617H14=A-PU Resin (Polytol Component A 495 g); Material No. 617H14=B-isocyanate (Polytol Component B 99 g); and Material No. 617h14=C-Catalyst (Polytol Component C 165 g), all from Otto Bock Health Care, 2 Carlson Parkway North, Suite 100, Plymouth, Minn. 55447. Materials may also include, without limit, Epox-Acryl (Epoxy Vinyl Ester Resin), Product Code EA1, from Foresee Orthopedic Products, 693 Hi Tech Pkwy, Oakdale, Calif. 95361; and Vibrathane B870, Vibracure A170, and Vibracure C070, all from Chemtura Corporation, 199 Benson Road, Middlebury, Conn. 06749.

Illustratively, in a sealed chamber under sub-atmospheric pressure, any attempt of the residual limb to move away from the socket wall creates an immediate increase in sub-atmospheric pressure in that area. In repetitive and prolonged time periods under this increased pressure, capillary filling, blistering, and bleeding may occur, causing tissue damage. This can happen during weight bearing, partial weight-bearing, or non-weight bearing sitting. Any inability of the socket to maintain its intimate relation with the residual limb sets up the high pressure areas.

In the present invention, the mobility of the inner socket combined with the sub-atmospheric pressures with the socket 50 allows the variable response of inner socket 50 to maintain a constant compliant relationship with the residual limb as it changes shape during range of motion and vertical tangential and rotational loads, thereby minimizing low pressure differences.

2. Single Socket with Flexible Brim.

FIG. 5 illustrates a second embodiment of the subject invention. The embodiment in FIG. 5 differs from that of FIG. 4 in that only a single, rigid outer socket 70 is used, rather than two sockets. Also, the rigid outer socket 70 further comprises a stiffer portion 74 and a less stiff portion 76 proximate the brim 78. The stiffness of the socket 70 may transition smoothly between the stiffer portion 74 and the less stiff portion 76.

The stiffness of the flexible brim portion 78 of the outer socket 70 is sufficient to: 1) reduce the sharp high pressure line seen when the limb is driven against the rigid brim of previous designs and 2) follow the limb when it is pulled away from the socket. The stiffness of the flexible brim of the socket 70 is matched to the pressure differential force that holds the brim against the liner or limb.

The force (F) that tends to hold the flexible brim against the liner 30 or limb 6 is a function of the size of the suspension vacuum P. This is the same as saying the difference in the absolute pressures on either side of the flexible brim: (1 atm—low pressure in the socket). This force is also a function of the area of the flexible brim. In equation form:

$$F = AP$$

Where F=pressure differential force holding the flexible brim to the liner or limb.

A=area of the portion of the flexible brim being considered.

P=suspension vacuum.

If P=10 psi and A=1 in², F=10 lbs.

The flexible brim stiffness (M=bending moment) is then matched to this force so that the flexible brim is able to follow the liner or limb. This is done by selecting any combination of brim materials (elastic modulus) and brim thicknesses (area of moment of inertia) that will allow the pressure differential force F to flex the brim (curvature) to the amount needed to follow the liner and limb. The equation for stiffness M is:

$$M = EIk$$

Where E=elastic modulus (Young's modulus) of the socket brim material.

I=area moment of inertia ("thickness" of brim material)

k=curvature (amount of brim bending).

Unless otherwise defined, all technical and scientific terms used herein have the same meaning as commonly understood by one of ordinary skill in the art to which this invention belongs. Although methods and materials similar to or equivalent to those described herein can be used in the practice or testing of the present invention, suitable methods and materials are described below. All publications, patent applications, patents, and other references mentioned herein are incorporated by reference in their entirety to the extent allowed by applicable law and regulations. In case of conflict, the present specification, including definitions, will control.

The present invention may be embodied in other specific forms without departing from the spirit or essential attributes thereof, and it is therefore desired that the present embodiment be considered in all respects as illustrative and not restrictive, reference being made to the appended claims rather than to the foregoing description to indicate the scope of the invention.

What is claimed:

1. A socket system in an artificial limb for amputees having a residual limb, the socket system being vacuum-managed and dynamically activated by weight-bearing loads and variable in response to shear forces imposed by weight-bearing loads, the socket system comprising:
    (a) a liner adapted to engage the residual limb;
    (b) an inner socket having a textured surface;
    (c) an inner socket air wick between the liner and the inner socket;
    (d) an outer socket having a textured surface;
    (e) an outer socket air wick between the inner socket and the outer socket;
    (f) a sealing sleeve engaging the outer socket and for engaging the residual limb, creating a sealed chamber enclosing the outer socket, the outer socket air wick, the inner socket, and the inner socket air wick;
    (g) a vacuum source connected to the sealed chamber and creating a vacuum within the sealed chamber, said vacuum drawing the inner socket air wick against the textured surface of the inner socket and the outer socket air wick against the textured surface of the outer socket;
    (h) wherein the socket system is dynamically activated in response to weight bearing loads and has a variable response to vertical, tangential, and rotational forces imposed by the weight bearing loads, thereby minimizing vacuum pockets or voids within the system, distributing shear forces evenly over the residual limb, and maintaining total contact between the residual limb and the socket system.

2. The socket system of claim 1, wherein the inner socket is more flexible than the outer socket.

3. The socket system of claim 2, wherein the textured surface of the inner socket increases the coefficient of sliding friction between the inner socket and the inner socket air wick and wherein the textured surface of the outer socket increases the coefficient of sliding friction between the outer socket and the outer socket air wick.

4. The socket system of claim 1, wherein the inner socket further comprises an inner surface facing the liner, and wherein the textured surface of the inner socket is on the inner surface.

5. The socket system of claim 1, wherein the inner socket further comprises an outer surface facing the outer socket, and wherein the textured surface of the inner socket is on the outer surface.

6. The socket system of claim 1, wherein the liner further comprises a textured surface facing the inner socket.

7. A method of vacuum-managing and dynamically activating and varying the response of a socket system for an artificial limb for amputees having a residual limb, the socket system comprising an inner socket, an inner socket air wick, an outer socket, an outer socket air wick, and a seal, the seal creating a vacuum chamber enclosing the inner socket, the inner socket air wick, the outer socket, and the outer socket air wick, comprising the steps of:
    (a) providing a textured surface on the inner socket facing the inner socket air wick in order to vary the coefficient of sliding friction between the inner socket and the inner socket air wick;
    (b) providing a textured surface on the outer socket facing the outer socket air wick in order to vary the coefficient of sliding friction between the outer socket and the outer socket air wick; and
    (c) creating a vacuum in the vacuum chamber, thereby dynamically adhering the inner socket air wick to the inner socket and the outer socket air wick to the outer socket.

8. The method of claim 7, further comprising a step of calculating the necessary coefficients of sliding friction based on the amputee's body weight, the surface area of the amputee's residual limb, the surface areas of the inner and outer sockets, and the vacuum pressure in the vacuum chamber.

9. The method of claim 7, further comprising a step of varying the vacuum pressure in the vacuum chamber to compensate for weight-bearing loads and tangential and rotational forces within the socket system.

10. The method of claim 7, further comprising the step of varying the flexibility of the inner socket and the outer socket at the time of manufacture.

11. The method of claim 7, further comprising the step of varying the surface area of the textured surfaces at the time of manufacture.

12. The method of claim 7, further comprising the step of varying the coefficient of sliding friction of the textured surfaces at the time of manufacture.

13. The method of claim 7, further comprising a step of providing a textured surface on the inner socket facing the outer socket air wick in order to vary the coefficient of sliding friction between the inner socket and the outer socket air wick.

14. The method of claim 7, further comprising a step of providing a textured surface on the liner facing the inner socket air wick in order to vary the coefficient of sliding friction between the liner and the inner socket air wick.

* * * * *